United States Patent [19]

de Ruiter

[11] Patent Number: Plant 7,051

[45] Date of Patent: Oct. 31, 1989

[54] MINIATURE ROSE PLANT

[75] Inventor: Gijsbert de Ruiter, Hazerswoude, Netherlands

[73] Assignee: de Ruiter's Nieuwe Rozen B.V., Netherlands

[21] Appl. No.: 245,008

[22] Filed: Sep. 15, 1988

[51] Int. Cl.[4] ..... A01H 5/00

[52] U.S. Cl. ..... Plt./9

[58] Field of Search ..... Plt. 9, 7

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new variety of miniature rose having light pink flowers produced on a good pot forcing plant.

2 Drawing Sheets

SUMMARY OF THE INVENTION

The present invention relates to a new and distinct variety of rose plant of the miniature rose class, which was originated by my crossing as seed and pollen parents two unnamed, unpatented seedlings of my creation. The varietal denomination of this new rose is "Ruimissa".

Among the novel characteristics possessed by this new variety which distinguishes it from its parents and all other varieties of which I am aware are its attractive light pink flowers borne on a plant particularly suited for production of flowering pot plants and that can also be reproduced through propatation by cuttings. Flowers of the new variety are long lasting on the plant. Asexual reproduction by budding and by propagation by cuttings of the new variety as performed in Hazerswoude, Holland, shows that the foregoing and other distinguishing characteristics come true to form and are established and transmitted through succeeding propagations.

The accompanying drawings shown typical specimens of the vegetative growth and flowers of the new variety in different stages of development and as depicted in color as nearly true as it is reasonably possible to make the same in a color illustration of this character.

BRIEF DESCRIPTION OF THE DRAWINGS

FIG. 1 is an illustration of the flowering plant of the new variety of miniature rose showing plant habit but with non-typical flower coloring; and FIG. 2 is an illustration showing details of the new miniature rose variety with flower coloring more nearly typical of plants grown indoor under glass.

DESCRIPTION OF PREFERRED EMBODIMENT

The following is a detailed description of my new variety, with color terminology in accordance with The Royal Horticultural Society Color Chart (R.H.S.C.C.) and horticultural terminology in accordance with standard terminology used in UPOV-approved horticultural guidelines. The terminology used in color description herein refers to plate numbers in the aforementioned color chart, e.g., "49A" is plate 49A of The Royal Horticultural Society Color Chart.

Parentage: Seedling.

*Seed parent.*—Unnamed seedling.

*Pollen parent.*—Unnamed seedling.

Class: Miniature.

As can be seen in the accompanying illustrations, FIG. 1 shows one sample of flowering plant of "Ruimissa" depicting the pot plant habit of growth and flowering. Since flowering is nearly continuous, the floreferous "Ruimissa" pot plant can remain attractively in bloom for long periods when given proper indoor care and culture.

FIG. 2 shows details of the new variety "Ruimissa". In the illustration there is shown the top of a young shoot 1; a green bud 2; a flower bud 3 after sepals separate; a flower bud 4 after sepals fall; a flower 5 about one-half open; and a bloom 6 fully open. Also shown are a flower stem 7 with reproductive organs but without petals, a flower stem 8 as in 7 but without stamens and, 9 the same but additionally without sepals. FIG. 2 further shows a branch and side branch 10 and a branch with thorns 11. Examples of the foliage may be seen as compound three, five, and seven leaflet leaves 12, 14 and 13, respectively.

The following further horticultural observations were made of specimens grown under glass in Hazerswoude, Holland.

FLOWER

Blooming habit: Nearly continuous.

A. Bud:

(1) *Size.*—Medium.

(2) *Form.*—Pointed.

(3) *Color.*—As sepals divide, bud color is near 50A to 49A with yellow coloring toward base.

(4) *Sepals.*—Longer than bud, slightly foliated.

(5) *Peduncle.*—Length — about 2 to 3 cm. Aspect — straight. Strength — erect. Color — near 141B.

B. Bloom:

*Flower.*—Average size for miniature; viewed from top — irregularly rounded; viewed from side; (A) upper part of fully opened flower — convex; (B) lower part of fully opened flower — flat convex.

(1) *Size.*—Average size when fully expanded — about 2.5 to 3 cm.

(2) *Borne.*—Primarily, singly, one to a stem.

(3) *Form.*—Ovoid at first, becoming flat. Outer petals reflex and quill; inner petals roll under.

(4) *Petalage.*—Number of petals under normal conditions — about 20 to 24, fully double.

(5) *Color.*—After sepals fall and petals unfurl, predominant flower color viewing petals' top surface is near 48A to B. Color through this range is substantially stable. Petals are imbued with yellow underlay toward point of petal attachment approaching near 1C and near 4D on the petals top and undersurfaces, respectively, at the point of petal attachment. Overall tonality from a distance is an attractive pink.

C. Petals:

(1) *Texture.*—Medium to thick.

(2) *Appearance.*—Inside velvety and outside satiny.

(3) *Form.*—Obovate.

(4) *Arrangement.*—Regularly arranged, imbricated.

(5) *Petaloids in center.*—Few.

(6) *Persistence.*—Drop off cleanly.

(7) *Fragrance.*—Slight to none.

(8) *Lasting quality.*—Very long lasting quality on plant.

REPRODUCTIVE ORGANS

A. Stamens, filaments and anthers:

*Arrangement and color.*—Regularly arranged around styles. Color — filaments orange yellow.

B. Pollen:

*Color.*—Yellow

C. Styles: Even, medium length, bunched

D. Stigmas: Full.

E. Hips: None observed.

PLANT

A. Form: Bushy.

B. Growth: Vigorous.

*Height attained.*—About 20 to 30 cm.

C. Foliage: Compound 3, 5 and 7 leaflets (1) *Size.*—Medium for a miniature.

(2) *Quantity.*—Abundant.

(3) *Color.*—Foliage at time of first flowering — medium to dark green.

(4) *Shape.*—Oval, pointed.

(5) *Texture.*—Upper side is semi glossy; Under side is matte.

(6) *Edge.*—Serrate.

(7) *Serration.*—Ordinary, acuminate apices.

(8) *Leaf stem.*—Color — medium to dark green (9) *Stipules.*—Medium length, slightly bearded, light green, distinct auricle.

(10) *Leaflet.*—Cross section — flat terminal. Terminal leaflet — very short, narrow, rounded base. Petiole — medium.

D. Wood:

(1) *New wood.*—Color — pale green.

(2) *Old wood.*—Color — medium green.

E. Prickles (thorns):

(1) *Prickles.*—Quantity (main stalk) — ordinary. On laterals from stalk — few. Form — straight and slanted slightly downward. Length — >5 mm. Color — tan to light pale green. Position — irregular.

(2) Bristles and glandular hairs: Few.

F. Winter hardiness: Needs protection outdoors in severe climates.

I claim:

1. A new and distinct variety of rose plant of the miniature rose class, substantially as shown and described, characterized particularly by a plant suitable for growing in pots and by attractive light pink flowers which are long lasting on the plant.

* * * * *

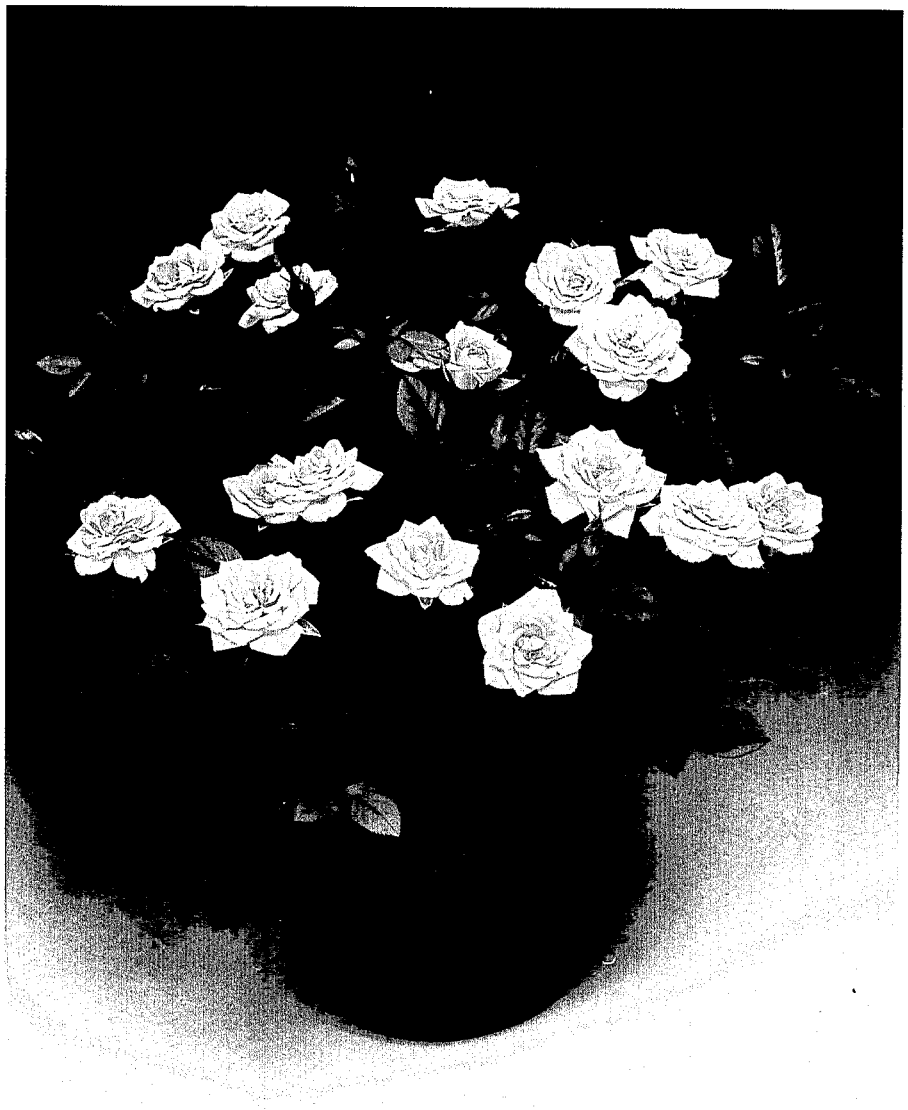
(var. Ruimissa)

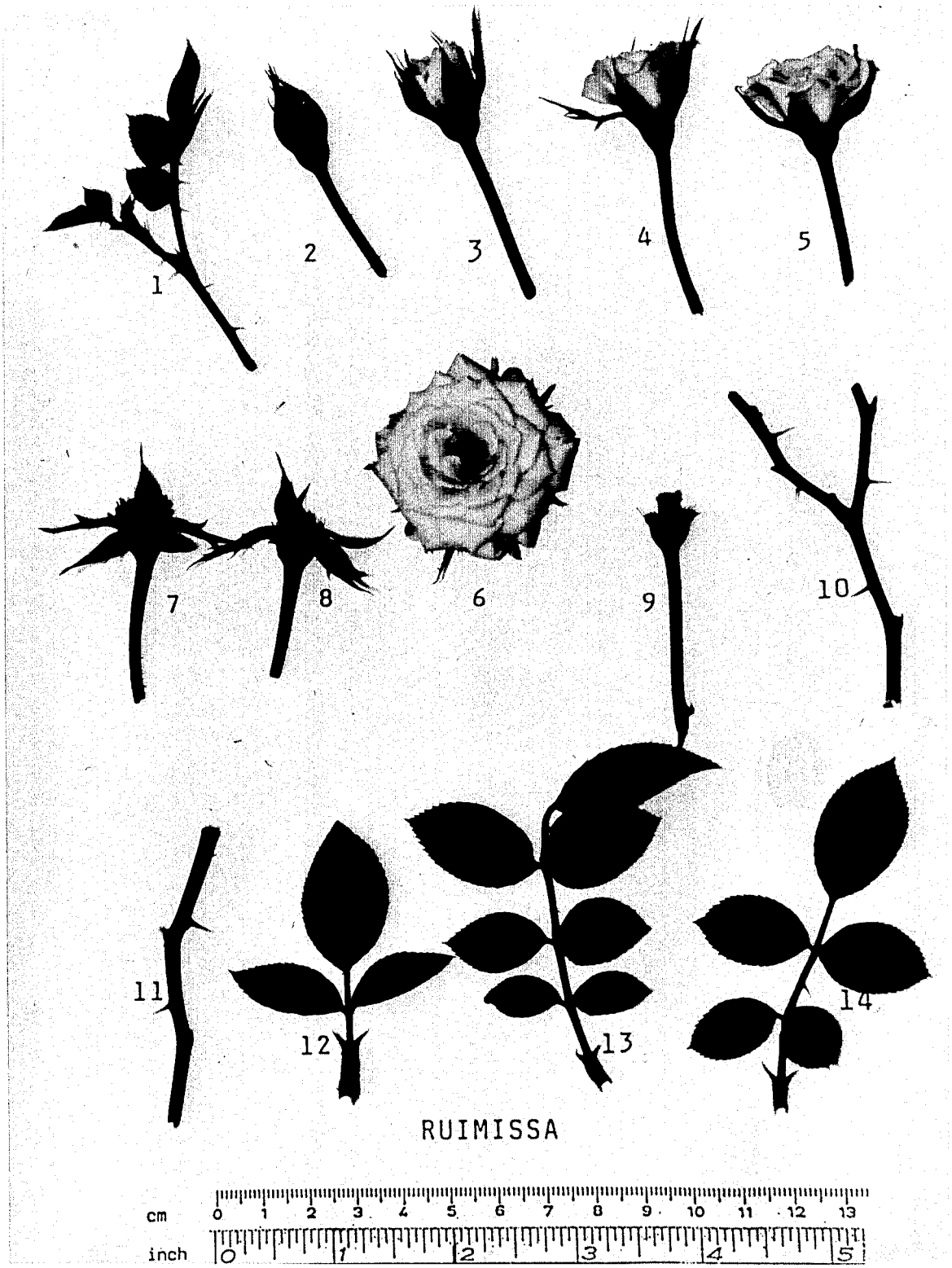
1
2
3
4
5
6
7
8
9
10
11
12
13
14
RUIMISSA
cm
0 1 2 3 4 5 6 7 8 9 10 11 12 13
inch
0 1 2 3 4 5